United States Patent
Luzon et al.

(10) Patent No.: US 8,702,772 B2
(45) Date of Patent: Apr. 22, 2014

(54) DEVICE FOR DERMATOLOGICAL USE WITH A FAILSAFE CONTROL

(75) Inventors: Josef Luzon, Bet Yehoshua (IL); Martin Gurovich, Tel Aviv (IL)

(73) Assignee: Derma Dream Group Ltd., Tortola (VG)

( * ) Notice: Subject to any disclaimer, the term of this patent is extended or adjusted under 35 U.S.C. 154(b) by 0 days.

(21) Appl. No.: 13/609,418

(22) Filed: Sep. 11, 2012

(65) Prior Publication Data
US 2014/0074193 A1    Mar. 13, 2014

(51) Int. Cl.
*A61N 5/06* (2006.01)
*A61B 5/00* (2006.01)
*A61B 18/00* (2006.01)

(52) U.S. Cl.
CPC ......... *A61B 5/44* (2013.01); *A61B 2018/00648* (2013.01)
USPC ............................................................ 607/89

(58) Field of Classification Search
CPC ........... A61B 2018/00648; A61B 2018/00642; A61B 2018/00666; A61B 2018/00904; A61B 2562/0257; A61B 5/443
See application file for complete search history.

(56) References Cited

U.S. PATENT DOCUMENTS

| | | | |
|---|---|---|---|
| 2005/0251118 A1* | 11/2005 | Anderson et al. | 606/9 |
| 2008/0004611 A1* | 1/2008 | Houbolt et al. | 606/9 |
| 2009/0112297 A1* | 4/2009 | Fiset | 607/91 |
| 2012/0191021 A1* | 7/2012 | Sobol et al. | 601/15 |
| 2012/0283803 A1* | 11/2012 | Liu et al. | 607/89 |

\* cited by examiner

*Primary Examiner* — Gary Jackson
*Assistant Examiner* — Scott T Luan
(74) *Attorney, Agent, or Firm* — Pearl Cohen Zedek Latzer Baratz LLP

(57) ABSTRACT

A device and method for dermatological use with one or a plurality of active components and a failsafe control. The device includes a light source configured to be toggled between an activated state and an inactivated state, a photosensitive detector configured to detect incoming light and a processing unit for the failsafe control. The processing unit is configured to concurrently determine whether light detected by the photosensitive detector is indicative of a safe operating proximity and is indicative of a safe operating skin tonal range; and activate the active components only when the processing unit determines that the device is within the safe operating proximity, and that the light reflected from the surface is indicative of the safe operating proximity and safe operating skin tonal range.

20 Claims, 8 Drawing Sheets

DEVICE FOR DERMATOLOGICAL USE WITH A FAILSAFE CONTROL

FIELD OF THE INVENTION

The present invention relates to devices and methods for dermatological uses. In particular the invention relates to a device for dermatological use, the device including a failsafe control.

BACKGROUND OF THE INVENTION

In intense Pulsed Light treatments (IPL) and laser treatments, pulses of light may be used for medical therapeutic and cosmetic treatments. Customizable wavelengths of light may be targeted at particular chromophores in skin to deal with cosmetic and dermatological concerns and therapies.

These treatments may include acne, photorejuvenation, treatment of instances of telangiectasia and rhytids, and in the treatment of dyschromia, i.e., to eliminate freckling, dark spots, sun damage, unsightly capillaries, pigmented and vascular lesions, rosacea, and other blemishes. Typically both medical and clinical treatment may result in minimal to no affect to normal skin. In some instances IPL may be used for hair removal, as distinct from electrolysis.

Outputs of IPL machines or laser based machines, typically high intensity light that may include polychromatic non-coherent light over a broad wavelength spectrum, may typically include wavelengths from 330 nm to 1200 nm or specifically selected wavelengths. Often the wavelength and energy (joules/unit of area) of the treatment may be dependent on the nature of the treatment, e.g., medical grade or cosmetic/salon grade, and the condition to be treated.

SUMMARY OF THE INVENTION

There is thus provided in accordance with some embodiments of the present invention a device for dermatological use with one or a plurality of active components and a failsafe control, the device may include a light source configured to be toggled between an activated state and an inactivated state, a photosensitive detector configured to detect incoming light and a processing unit for the failsafe control. The processing unit may be configured to concurrently determine whether light detected by the photosensitive detector is indicative of a safe operating proximity of the device to a surface, determine whether light reflected from the surface and detected by the photosensitive detector is indicative of a safe operating proximity of the device to the surface, and determine whether light reflected from the surface and received by the photosensitive detector is indicative of a safe operating skin tonal range. The processor may be further configured to activate the active components only when the processing unit determines that the device is within the safe operating proximity, and that the light reflected from the surface is indicative of the safe operating proximity and safe operating skin tonal range.

Furthermore, in accordance with some embodiments of the present invention, the photosensitive detector for detecting light indicative of a safe operating proximity of the device to the surface, the photosensor detector for detecting light reflected from the surface indicative of a safe operating proximity, and the photosensor detector for detecting light reflected from the surface and indicative of a safe operating skin tonal range is a single photosensor detector.

Furthermore, in accordance with some embodiments of the present invention, a single light source may provide both the light reflected from the surface and detected by the photosensitive detector for determining a safe operating proximity of the device to the surface, and the light reflected from the surface and received by the photosensitive detector for determining a safe operating skin tonal range.

Furthermore, in accordance with some embodiments of the present invention, a trigger may be configured to be depressed and/or otherwise activated before the processing unit determines whether light reflected from the surface and received by the photosensitive detector is indicative of a safe operating skin tonal range.

Furthermore, in accordance with some embodiments of the present invention, a trigger may be configured to be depressed and/or otherwise activated within a set temporal period before the processing unit determines whether light reflected from the surface and received by the photosensitive detector is indicative of a safe operating skin tonal range.

Furthermore, in accordance with some embodiments of the present invention, activating the active components may result in the device delivering a set of pulses of energy to the surface.

Furthermore, in accordance with some embodiments of the present invention, the processing unit for the failsafe control may be further configured, after activating the active components, to determine again whether light detected by the photosensitive detector is indicative of a safe operating proximity of the device to a surface, whether light reflected from the surface and detected by the photosensitive detector is indicative of a safe operating proximity of the device to the surface, and whether light reflected from the surface and received by the photosensitive detector is indicative of a safe operating skin tonal range before activating the active components again.

Furthermore, in accordance with some embodiments of the present invention, the processing unit for the failsafe control may be further configured, after activating the active components, to determine whether light detected by the photosensitive detector is indicative of a safe operating proximity of the device to a surface and determine whether light reflected from the surface and received by the photosensitive detector is indicative of a safe operating skin tonal range before activating the active components again.

Furthermore, in accordance with some embodiments of the present invention, the processing unit for the failsafe control may be configured to determine whether light reflected from the surface and received by the photosensitive detector is indicative of a safe operating skin tonal range and concurrently determine whether light detected by the photosensitive detector is indicative of a safe operating proximity of the device to a surface and determine whether light reflected from the surface and detected by the photosensitive detector is indicative of a safe operating proximity of the device to the surface.

Furthermore, in accordance with some embodiments of the present invention, the processing unit for the failsafe control may be configured to iteratively determine whether light reflected from the surface and received by the photosensitive detector is indicative of a safe operating skin tonal range, and concurrently determine whether light detected by the photosensitive detector is indicative of a safe operating proximity of the device to a surface and determine whether light reflected from the surface and detected by the photosensitive detector is indicative of a safe operating proximity of the device to the surface.

Furthermore, in accordance with some embodiments of the present invention, the device may be configured for home use.

Furthermore, in accordance with some embodiments of the present invention, the device may be configured for cosmetic use.

Furthermore, in accordance with some embodiments of the present invention, the active component may be configured to provide intense pulsed light therapy.

Furthermore, in accordance with some embodiments of the present invention, the active component may be configured to provide laser therapy.

There is further provided in accordance with some embodiments of the present invention a method for use of a device for dermatological use with one or a plurality of active components and a failsafe control, the method including configuring a light source to be toggled between an activated state and an inactivated state, configuring a photosensitive detector to detect incoming light and configuring a processing unit. The processing unit configured to concurrently determine whether ambient light detected by the photosensitive detector is indicative of a safe operating proximity of the device to a surface, determine whether light reflected from the surface and received by the photosensitive detector is indicative of a safe operating distance from the surface and determine whether light reflected from the surface and received by the photosensitive detector is indicative of a safe operating skin tonal range. The processing unit activating the active components only when the processing unit determines that the device is within the safe operating proximity, and that the light reflected from the surface is indicative of the safe operating skin tonal range.

Furthermore, in accordance with some embodiments of the present invention, the device may be configured for home use.

Furthermore, in accordance with some embodiments of the present invention, the device may be configured for cosmetic use.

Furthermore, in accordance with some embodiments of the present invention, the active component may be configured to provide intense pulsed light therapy.

Furthermore, in accordance with some embodiments of the present invention, the active component may be configured to provide laser therapy.

There is further provided in accordance with some embodiments of the present invention A failsafe control for a device, the failsafe control including a light source, the light source configured to be togglable to an activated and inactivated state, a photosensitive detector configured to measure ambient lighting and reflections, a processing unit configured to activate the device when ambient lighting and reflections indicate a safe operation of the device, and the processing unit may be further configured to deactivate the device when ambient lighting or reflections indicate an unsafe operation of the device.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

Figure 1:
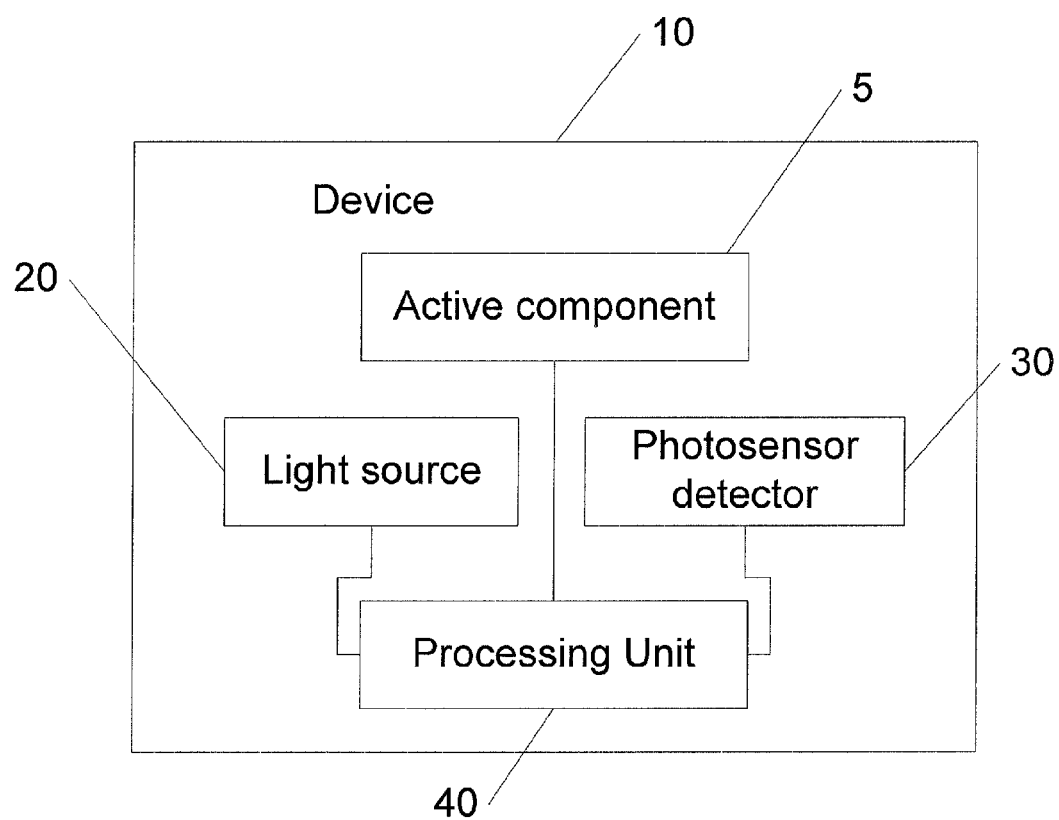
FIG. 1 is a schematic illustration of a device for dermatological use, with a failsafe control, according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the methods and apparatus. However, it will be understood by those skilled in the art that the present methods and apparatus may be practiced without these specific details. In other instances, well-known methods, procedures, and components have not been described in detail so as not to obscure the present methods and apparatus.

Although the examples disclosed and discussed herein are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method examples described herein are not constrained to a particular order or sequence. Additionally, some of the described method examples or elements thereof can occur or be performed at the same point in time.

Unless specifically stated otherwise, as apparent from the following discussions, it is appreciated that throughout the specification, discussions utilizing terms such as "adding", "associating" "selecting," "evaluating," "processing," "computing," "calculating," "determining," "designating," "allocating" or the like, refer to the actions and/or processes of a computer, computer processor or computing system, or similar electronic computing device, that manipulate, execute and/or transform data represented as physical, such as electronic, quantities within the computing system's registers and/or memories into other data similarly represented as physical quantities within the computing system's memories, registers or other such information storage, transmission or display devices.

Light and/or other forms of radiation may be employed in the medical and/or cosmetic industries for treating skin or other cosmetic or cosmetic related conditions. Under the theory of photothermolysis, pulsed light of specific wavelengths and duration directed at specific chromophores within a specific tissue may destroy or sufficiently alter those chromophores. The destruction or sufficient alteration of chromophores may result in medical and/or cosmetic benefits without significantly harming and/or affecting surrounding tissue.

In particular, intense pulse light therapy, laser therapy and/or other therapies that may emit energy, radiation and/or other therapeutics may be used for cosmetic and/or medical repair and may involve the use of one or a plurality of xenon flash lamps, lasers and, in some examples, capacitors, the flash lamps, lasers and capacitors may be contained within an articulated arm, handheld device, or other types of delivery devices.

The delivery devices may have variable specifications. The variable specifications may include light sources that may be configurable to deliver a full spectrum or a filtered spectrum of light. For example, the devices may also include filters that are used for narrowing and/or selecting particular wavelengths of light, the wavelengths typically ranging from 400 to 1400 nm for an IPL device and specific wavelengths for laser devices.

In particular, these different wavelengths may be employed by a light therapy device 10 depending on, and in some examples, optimized for the target. In some examples, a wavelength of 410 nm may be used to target acne; a wavelength of 530 nm may be used to target pigmented lesions, a wavelength of 560 nm may be used for photorejuvination; a wavelength of 690 nm may be used for some forms of hair removal and/or reduction. Other wavelengths for other treatments may also be available and efficacious.

The devices may have variable energy settings, i.e., fluencies: the amount of energy delivered per unit of area, typically measured in joules per square centimeter. In some examples the fluence of a light therapy device, for example and IPL device, may range from a few joules/cm² to 40+ joules/cm². In some examples, a device may employ a different range.

In some embodiments of the invention, devices, including intense pulse light therapy devices, may include variable pulse durations of light, in some examples, the duration of the pulse may be from 5 to 30 milliseconds. In some examples, the duration of pulsed light may be from 0.2 to 100 milliseconds, delivered as single, double, triple, and other types of pulses.

Intense pulse light therapy may involve single or multiple pulses of high intensity light from the xenon lamps, rapidly discharged to a surface of the skin of a user. In some examples, selected wavelengths of the light, rapidly discharged, will travel through the surface of the skin until the desired chromophore is hit. In some examples, the pulsed light of the xenon lamp may be converted to heat energy where it may coagulate a targeted cell type within the skin of the user.

In some examples, a hood may be employed to limit the escape of light from a light therapy device 10 into the surrounding areas. The hood may be square or rectangular or of other geometric designs including a plain cylindrical or conical and or other geometrical patterns and designs.

The use and efficacy of intense pulse light and/or laser therapy may be related to a user's skin pigmentation. In some examples the user's skin type, e.g., the skin tonal range, reflecting different make-ups of skin pigmentation, may be distinguishable as one of 6 options on the Fitzpatrick scale described below.

Home use devices, e.g., not clinic based devices, or devices intended for the lay public may include intense pulsed light therapy (IPL) and laser therapy devices and may use safety features including one or a plurality of failsafe devices, employing the one or a plurality of failsafes, to prevent injury to a user or to other individuals. In particular, home use devices may be designed to prevent the flashing of light too far from a surface, e.g., the surface of the skin intended to be treated or acted upon. In some embodiments of the invention, home use devices may be designed with a failsafe control to prevent the use of light therapy on skin tones or skin pigmentation outside of a safe operating range, the operating range may be related to the wavelength of light, the fluence of the active component, e.g., a xenon lamp and/or laser, and other considerations.

In some examples, home use light therapy devices may use less energy, have fewer energy settings, a fixed pulse duration, a single fixed wavelength filter, smaller treatment areas, fewer cooling options, and usable on a narrower variation of skin pigmentations, and/or skin tonal ranges than what may be available under the guidance of a trained professional in a clinic or other professional or professional-like setting.

In some instances, a light therapy device or another device, including other devices for medical and/or cosmetic treatments, including medical and/or cosmetic treatment of skin, may use light sensors, including ambient light sensors. Ambient light sensors may be multifunctional light sensors that may have additional functions.

Ambient light sensors may be photo-sensitive components, peripheral electronics, peripheral logics and or other components that may be configured to measure ambient light (e.g., indoors and/or outdoors). The measurements may be used to configure different parameters of a device. Ambient light sensors may be active and/or passive components.

In some instances, a light therapy device, and/or another device, including other devices for medical and/or cosmetic treatments, including medical and/or cosmetic treatment of skin, may use a proximity sensor. The proximity sensor may be the same or similar to the ambient light sensor described above. In some embodiments of the invention, the proximity sensor and the ambient light sensor may both be the same photosensitive detector, as described below.

A proximity sensor may be able to detect a nearby object, or multiple nearby objects, without necessarily physically contacting those objects.

In some examples, a proximity sensor may emit an electromagnetic field, beam, or pulse of energy. In some embodiments of the current invention, the proximity sensor may be coupled to a device that emits an electromagnetic field, beam, or pulse that may be measured by proximity sensor. The electromagnetic field, beam or pulse may include light. The light may be in the visible spectrum. The light may be in the non-visible spectrum, including infrared.

A proximity sensor, in response to an emitted electromagnetic field, beam or pulse, may be configured to assess changes in the electromagnetic field and/or the signal returning to the sensor, the changes may indicate the presence, location and in some instances characteristics of a target. In some examples, the nature of the target may necessitate different types of proximity sensors including inductive sensors, capacitive sensors, capacitive displacement sensors, Doppler effect sensors, eddy-current sensors, laser rangefinder sensors, magnetic sensors, passive optical sensors, passive thermal infrared sensors, photocell sensors, reflective sensors, radar sensors, reflection of ionizing radiation sensors, sonar sensors, touch-screens, elevator switches and automatic vehicle detection (light traffic, speed control) and/or other types of sensors.

Proximity sensors may be employed in car bumpers to detect distances for backing up and/or parting, ground proximity sensors for aviation, vibration sensors for rotating shafts within heavy machinery, camshaft sensors for reciprocating engines. sheet break sensors for printing machines, sensors for roller coasters, conveyors, mobile phones, electronics, small arms munitions, and other applications.

In some examples a proximity sensor may have a definable range of detection. The sensor may have a maximum distance for detecting the target, i.e., a nominal range. In some examples a nominal range may be adjusted or a graduated detection distance may be reportable.

In some examples, proximity sensors may not have moving mechanical parts. The lack of moving mechanical parts may make a proximity sensor more reliable and have a longer operating life than a similar product with moving mechanical parts.

Optical proximity sensors may be light beam sensors of the thru-beam type, retro reflective type or other types of sensors. In some examples, optical proximity sensors may pulse infrared or other forms of visible a non-visible light off and on at fixed frequencies. The frequencies may be known to other components of the proximity sensor, including measuring components. In some examples, when configured to detect pulsing with a known frequency, an optical sensor circuit may be designed such that light not pulsing at the pre-defined frequency is rejected.

Optical proximity sensors may be used in smart phones and other electronics in user-interactive and other applications. In some instances, an optical proximity sensor may be used to bypass/deactivate a "touch screen" or other touch sensitive components when the smart phone is close to the ear of a user, i.e., on a phone call, or inside the pocket of a user.

Optical proximity sensors may be active sensors; i.e., optical proximity sensors may include a light emitting component, the light typically in the non-visible spectrum, e.g., infrared and a photosensitive detector, the photosensitive detector may be used to measure the reflections the light on a nearby/in-contact object.

Light therapy devices for non-trained personnel may implement different approaches of proximity sensors to, for example, avoid eye damage or other forms of bodily damage. For example, light therapy devices for non-trained personnel may implement different approaches of proximity sensors to avoid eye damage or other forms of bodily damage by preventing the activation of the pulse on the "open air", e.g., not in proximity to treatable tissue, including skin.

In dermatological devices for use in cosmetic and medical therapies, including Light therapy devices, skin pigmentation and/or skin tone sensors may determine the skin pigmentation and/or the skin tonal range of a user, and use data related to skin pigmentation of a potential user to configure the nature and specifications of light employed by the light therapy device. In some examples, the use of skin pigmentation sensors may avoid applying high optical energies on dark tone skin wherein energy is absorbed by the skin and may cause burns, rather than targeting the hair or blood vessels intended for removal or repair.

Skin pigmentation and/or skin tonal range measurements may be calculated with relation to the Fitzpatrick Classification Scale. The Fitzpatrick Classification Scale was developed in 1975, as devised by Thomas Fitzpatrick. The Fitzpatrick Classification Scale may also be related to the Von Luschan's chromatic scale.

In the Fitzpatrick Classification Scale, a Type I pigmentation relates to a person who has a skin pigmentation that can be described as: white; very fair; freckles; typical albino skin and/or Celtic. Typically, a person with Type I pigmentation on the Fitzpatrick Classification Scale may have skin that never tans and always burns when unprotected and exposed to direct sunlight and/or other forms of light and or radiation. In the Von Luschan Chromatic Scale, a Type I individual typically has a score from 0-5, or in some calculations from 0-7.

In the Fitzpatrick Classification Scale, a Type II pigmentation relates to a person who has a skin pigmentation that can be described as: white; fair and/or light, or light-skinned European. Typically, a person with Type II pigmentation on the Fitzpatrick Classification Scale may have skin that tans with difficulty and usually burns when unprotected and exposed to direct sunlight and/or other forms of light. In the Von Luschan Chromatic Scale, a Type II individual typically has a score from 6-10, or in some calculations from 8-16.

In the Fitzpatrick Classification Scale, a Type III pigmentation may relates to a person who has skin pigmentation that can be described as: beige; very common, light intermediate, and/or dark-skinned European. Typically, a person with Type III pigmentation on the Fitzpatrick Classification Scale may have skin that gradually tans to a light brown color, but may sometimes result in a mild burn when unprotected and exposed for extended periods to direct sunlight and/or other forms of light. In the Von Luschan Chromatic Scale, a Type III individual typically has a score from 11-15, or in some calculations from 17-24.

In the Fitzpatrick Classification Scale, a Type IV pigmentation relates to a person who has skin pigmentation that can be described as beige with a brown tint, Caucasian, dark intermediate, Mediterranean or olive skinned. Typically, a person with Type IV pigmentation on the Fitzpatrick Classification Scale may have skin that rarely burns, tans with ease to a moderate brown when unprotected and exposed for extended periods to direct sunlight and/or other forms of light. In the Von Luschan Chromatic Scale, a Type IV individual typically has a score from 16-21 or in some calculations from 25-30.

In the Fitzpatrick Classification Scale, a Type V pigmentation relates to a person who has skin pigmentation that can be described as: dark brown. Typically, a person with Type V pigmentation on the Fitzpatrick Classification Scale may have skin that rarely burns and tans very easily when unprotected and exposed for extended periods to direct sunlight and/or other forms of light. In the Von Luschan Chromatic Scale, a Type V individual typically has a score from 22-28 or in some calculations over 30.

In the Fitzpatrick Classification Scale, a Type VI pigmentation relates to a person who has skin pigmentation that can be described as: very dark or black. Typically, a person with Type VI pigmentation on the Fitzpatrick Classification Scale may have skin that is deeply pigmented, never burns and tans very easily when unprotected and exposed for extended periods to direct sunlight and/or other forms of light. In the Von Luschan Chromatic Scale, a Type VI individual typically has a score from 29-36, or in some calculations over 30.

In some examples, a light therapy device may be configured to determine a users' Fitzpatrick Classification and/or Von Lushan Chromatic pigmentation, and/or skin tonal range, which may be a representative of these classifications and/or other classification methodologies, and adjust operation of the light therapy device accordingly.

FIG. 1 is a schematic illustration of a device for dermatological use, with a failsafe control, according to an embodiment of the invention.

One or a plurality of failsafe controls may be included in a device 10, configured to provide for safe operation of the device and to prevent unsafe operation of the device. In some embodiments of the invention, safe operation of the device may include operating the device within a given distance to a surface, e.g., a user's skin tissue, and only operating the device on a predefined range of skin tissues, the skin tissues may be defined by their pigmentation. In some embodiments of the invention, an unsafe operation of device 10 may include operating device 10 at an unsafe distance, e.g., too far from the surface of the user's tissue, and/or operating the device on tissue where the tissue may be harmed by the use of the device. In some examples the use of the device on a tissue may not be efficacious, given the tissue type and/or pigmentation.

Device 10 is a device configured to employ light or other forms of energy to tissue, including skin, for medical and/or cosmetic therapy and cosmetic use. Device 10 may be an IPL device. Device 10 may be a laser device. Device 10 may be a device that emits and/or pulses energy for therapeutic and/or cosmetic uses.

Device 10 may be configured for home use by a lay person without substantial training in the use of device 10. Device 10 may be configured for use in a clinic, spa or similar setting by a professional who may have some or substantial training related to device 10 or similar devices.

Device 10 provides therapy via different forms of energy for cosmetic, medical and/or therapeutic purposes. The energy may be emitted from an active component. The active component 5 may be a xenon flash bulb, in the case of an IPL device, and/or lasers, to provide laser therapy, other sources of light or energy may be used for other therapies.

Device 10 has one or a plurality of failsafe controls, these failsafe controls may include one or a plurality of light sources 20, photosensitive detectors 30 and/or processing units 40. In some embodiments of the invention, the processing unit may contain a processor, memory and/or other computational or computer related components. Other components of a light therapy device may be included in device 10.

Device 10 has an active component 5. Active component may be a source of energy, for example, light energy or laser energy. Active component 5 may provide the energy for the therapeutic, medical and/or cosmetic usage of device 10.

Light source 20 is configured to be in an activated state and in a deactivated state. In an activated state, light source 20 may be illuminated or otherwise providing light. In an inactivated state, light source 20 may not be illuminated or otherwise not providing light.

Light source 20 is toggable between an activated state and an inactivated state automatically, by processing unit 40 or by a user of device 10 or through other methods.

Photosensitive detector 30 may be configured to be an ambient light sensor, a proximity sensor and/or a detector of skin pigmentation. In some embodiments of the invention, photosensitive detector 30 may provide data for the determination of skin pigmentation or skin tonal range from reflections off of a surface.

Data from photosensitive detector 30 may be calculated by processing unit 40. Processing unit 40 may be configured to activate or inactivate active component 5 in response to data received from photosensitive detector 30.

In some embodiments of the invention, after device 10 detects close contact with an object, light therapy device 10 employs activated light source 20 and photosensitive detector 30 to determine that the object in close contact with device 10 is an actionable object, e.g., skin, and in some embodiments of the invention, the skin pigmentation and/or an actionable or safely actionable skin tonal range of the skin with which device 10 is in close contact with, e.g., the skin of a user. In some embodiments of the invention, this may be determined based on a level of reflection from the skin of the user as processed by processing unit 40.

Processing unit 40 may use data from photosensitive detector 30 to determine if skin tone of the user is within an allowed skin tonal range for a particular indication of device 10. The allowed range may be defined by efficacy of the light therapy device 10 vis-à-vis that skin tonal range, the energy of the light therapy device 10, and/or whether the light therapy device 10 may damage the skin, given the skin tone or due to other specifications.

Processing unit 40 may reject targets such as a garment or a piece of furniture or any other material that may be in contact with the device as not being skin and may prevent the activation of light therapy device 10.

In some embodiments of the invention, processing unit 40 may determine, based on measurements from photosensitive detector 30 that device 10 is in a proximity to an eye or other tissue, the other tissue may not be intended to be treated via IPL or other energy related treatments. When processing unit 40 determines that device 10 may be in proximity to an eye or other tissue, not be intended to be treated via IPL or other treatments, processing unit 40 may deactivate and/or not activate device 10.

According an embodiment of the disclosed invention, an ambient light sensor and a proximity sensor are the same physical components, e.g., photosensitive detector 10.

According to an embodiment of the invention, the light ambient sensor, the proximity sensor and the skin tone sensor are the same physical components, e.g., photosensitive detector 10.

Device 10 may provide a range of measurable radiant exposure, i.e., the amount of radiation delivered per unit area (fluence) of 1-100 j/cm$^2$. This range may be narrowed, in some embodiments of the invention, by one or a plurality of failsafe controls.

Device 10 may have a range of operational spectral emission wavelengths. This range in wavelengths may be related to the absorption spectra of the targeted chromophores and other biological targets. This range may be narrowed or changed, in some embodiments of the invention, by one or a plurality of failsafe controls.

Device may be configured to work with only specific tissue types, e.g., skin tissue. The skin tissue that device 10 may be configured to work with may be limited to specific skin pigmentations, or range of skin pigmentations e.g., an actionable skin tonal range. This range of specific skin pigmentations, or skin type measurements, may be described as from skin tones I through IV on the Fitzpatrick Classification Scale, described above. This range may be narrowed, in some embodiments of the invention, by one or a plurality of failsafe controls. The device may use other skin tonal ranges. A safe skin tonal range may be predetermined by the user and/or another entity.

In some embodiments of the invention, processing unit 40 may change, modify or otherwise alter one or a plurality of the aforementioned specifications of device 10, or other specifications, when a calculated proximity to a surface from the photosensitive detector measures of ambient lighting, and measures of skin pigmentation, and/or skin tonal range of the user indicate that specifications of the device might be altered for safety, efficacy or other indications.

In some embodiments of the invention, processing unit 40 may change, modify or otherwise alter one or a plurality of the aforementioned specifications of device 10, or other specifications, when a calculated proximity to a surface from the photosensitive detector measures of ambient lighting, and measures of skin pigmentation and/o skin tonal range of the user indicate a marginally safe skin tonal range, or a marginally safe proximity to tissue, e.g., skin tissue.

In some embodiments of the invention, processing unit 40 may change, modify or otherwise alter one or a plurality of the aforementioned specifications of device 10, or other specifications via an input from a user or another entity.

Figure 2A:
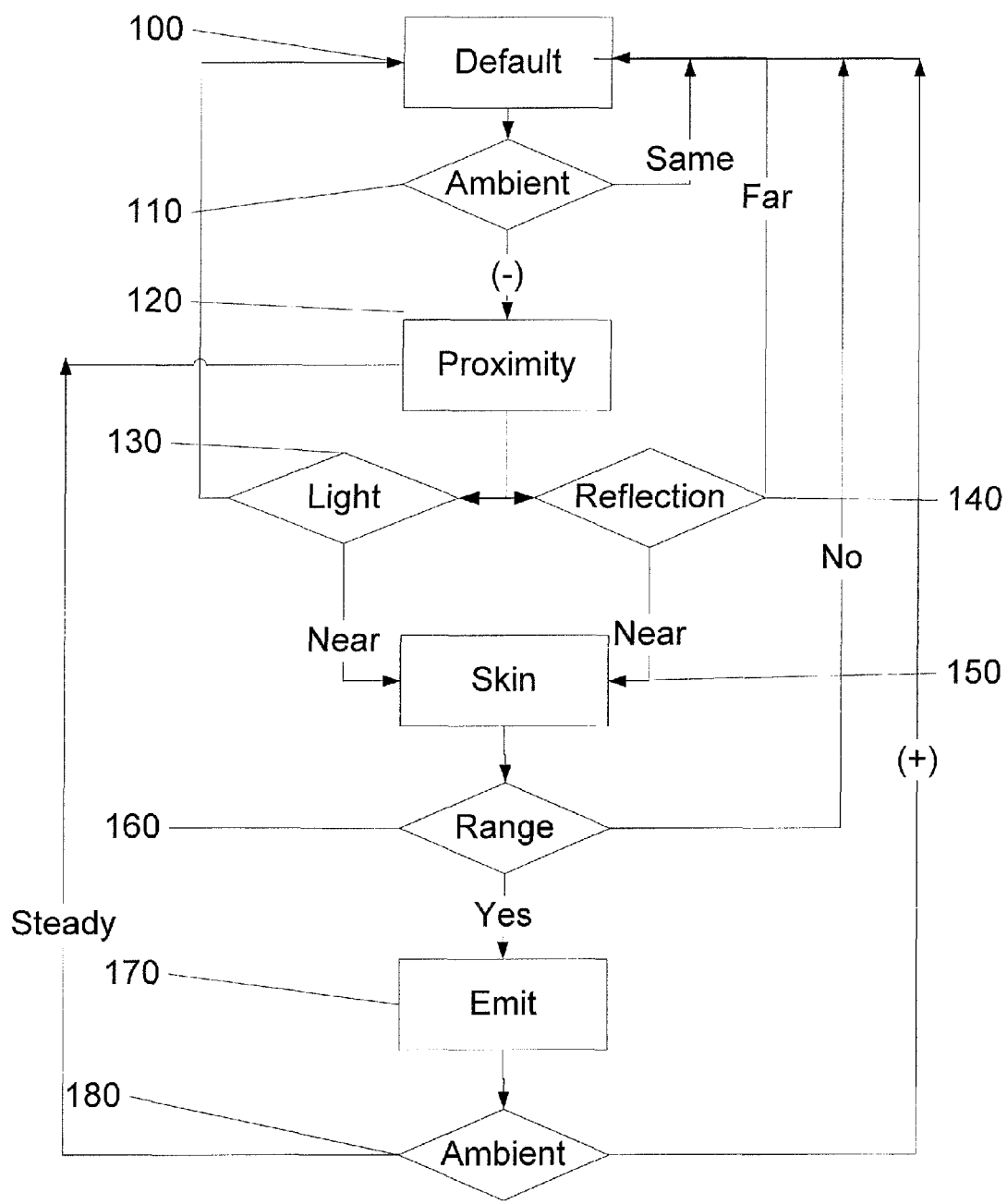
FIG. 2a is a schematic illustration of a method for using a device for dermatological use, with a failsafe control, according to an embodiment of the invention.

FIG. 2a is a schematic illustration of a method for a device for dermatological use, with a failsafe control, according to an embodiment of the invention.

In some embodiments of the invention, device 10 may be in a default state as depicted by box 100. In the default state of operation light source 20 is in a deactivated state. In the default stage, photosensor detector 30 may be configured to receive and/or measure ambient light as depicted by diamond 110.

If there is a significant reduction in ambient light, as determined by photosensitive detector 30 and/or processing unit 40, device 10 may enter into a proximity sensor state, as depicted by box 120. In some examples, the significant reduction may be a percentage of the average measured light in a previous time period, that previous time period may have a length of, for example, of 0.1-10 seconds. In some examples, the pervious time period may be longer; in some examples, the previous time period may be shorter.

If ambient light stays the same, or there is no significant reduction in ambient light, as determined by photosensitive detector 30 and/or processing unit 40, device 10 may remain in or reenter into the default state as depicted by box 100.

In proximity sensor state, light source 20 may in an inactive state. In proximity state with light source 20 in an inactive state, photosensor detector 30 may be configured to measure incoming light as depicted by diamond 130.

In proximity sensor state, light source 20 may be toggled to an active state. In proximity state with light source 20 toggled to an active state, photosensor detector 30 may be configured to measure reflected light. The reflected light may be light from light source 20, reflected off of a surface, for example, skin tissue of a user of device 10, as depicted by diamond 140.

If photosensor detector 30 and/or processing unit 40 measure no light, or in some examples, a small amount of light, the small amount of light may be calculated as described earlier with reference to box 120. In some examples, the small amount of light may be calculated with a different methodology.

If photosensor detector 30 and/or processing unit 40 measure a reflection off of a surface, the reflection indicative that the surface is near, then device 10 may enter proximity OK state, If photosensor detector 30 and/or processing unit 40 measure some light above a predefined threshold, and/or if photosensor detector 30 and/or processing unit 40 measure a reflection off of a surface, the reflection indicative that the surface is far, the distance being above a predefined threshold, then device 10 reverts back to default state 100. In some embodiments of the invention, a predefined threshold of a distance to the surface may be based on empirical data relating to the reflection of light, in some examples, from light source 20 on skin and/or on a range of skin pigmentation types. In some examples, a predefined threshold of a distance may be within a range of values, the range may be related to nature of a surface and the nature of light source 20.

In some embodiments of the invention, photosensor detector 30 and/or processing unit 40 may first measure the amount of light and then measure the distance of device 10 from the surface, given the reflection.

In some embodiments of the invention, photosensor detector 30 and/or processing unit 40 may first measure the distance indicated by the reflection and then measure the amount of light.

If Device 10 or a component thereof, determines that the values from photosensor detector 30 indicate that device 10 is operating within a proximity to a surface, the proximity may be predefined and may represent a safe operating distance, as indicated by measurements in diamond 130 and diamond 140, then device 10 may move to a skin pigmentation detection state, as depicted in box 150.

If device 10, or a component thereof, determines that photosensor detector 30 measures significant light, and/or photosensor detector 30 measures reflected light, the reflected light indicative of a proximity to a surface that is not a close operating proximity, then device 10 may move to default state 100.

The Skin pigmentation detection state, as depicted in box 150 may use the Fitzpatrick Classification Scale and/or the Von Luschan Chromatic Scale, or other methodologies, in analyzing skin pigmentation.

Light source 20 may be toggled to an active state. Photosensor detector 30 and/or processing unit 40 may be configured to determine whether reflected light from light source 20 off of a surface indicates that the surface may be skin tissue that falls within a predefined skin tonal range, as depicted by diamond 160.

If photosensor detector 30 and/or processing unit 40 determines that reflected light from light source 20 off of a surface indicates that the surface may be skin tissue that does not fall within a predefined skin tonal range, then device 10 may return to default state, as depicted by box 100.

If photosensor detector 30 and/or processing unit 40 determines that reflected light from light source 20 off of a surface indicates that the surface may be skin tissue that falls within a predefined skin tonal range, then one or a plurality of pulses of energy, e.g. light, may be emitted from device 10, as depicted by box 170.

After one or a plurality of pulses of energy, described above, are emitted from device 10, photosensor detector 30 and/or processing unit 40 may be configured to detect an increase in ambient or other lighting, the increase in lighting may be indicative of device 10 no longer in proximity to skin tissue of a user, as depicted by diamond 180.

If photosensor detector 30 and/or processing unit 40 detect an increase in ambient lighting, device 10 may return to the default state, as depicted by box 100.

If photosensor detector 30 does not detect an increase in ambient lighting device 10 may return to proximity state 120, described above. In some examples, if photosensor detector 30 does not detect an increase in ambient lighting for a predetermined amount of time, for example 0.1 to 5 seconds, device 10 may return to proximity state 120.

Figure 2B:
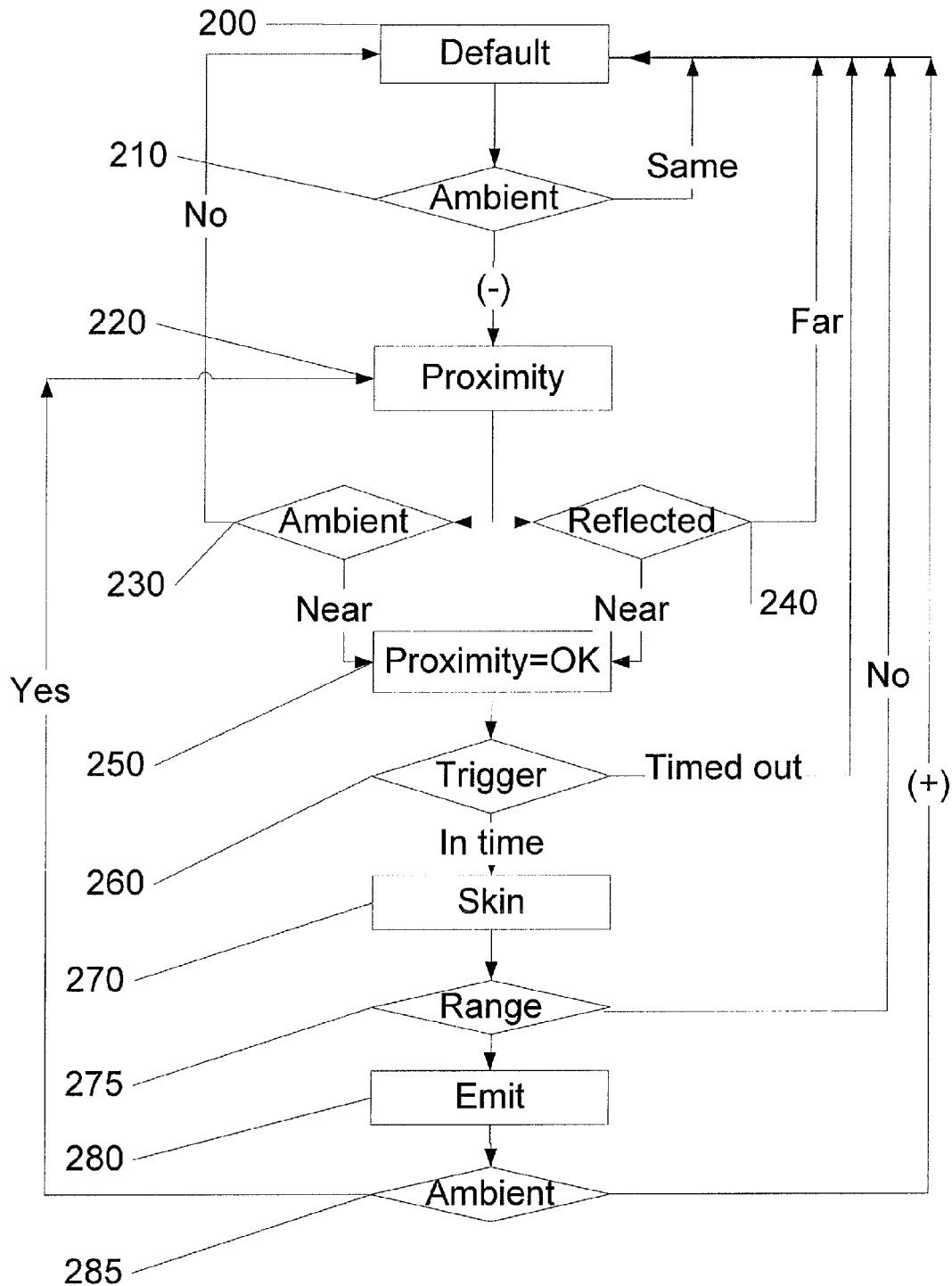
FIG. 2b is a schematic illustration of a method for using a device for dermatological use, with a failsafe control, according to an embodiment of the invention.

FIG. 2b is a schematic illustration of a method for a device for dermatological use, with a failsafe control, according to an embodiment of the invention.

Device 10 may be configured to be in a default state, as depicted by box 200. In the default state, light source 20 is toggled to the inactive state, as described above. In the default state, photosensor detector 30 is configured to monitor ambient lighting.

Photosensor detector 30 and/or processing unit 40 are configured to determine whether there has been a reduction, in some embodiments of the invention, a significant reduction, and in some embodiments of the invention, a total reduction in ambient lighting, as depicted in diamond 210.

If photosensor detector 30 and/or processing unit 40 determine that there has not been a significant reduction in ambient lighting, the reduction may be a predefined value, or may be a predefined range, device 10 remains in, and/or returns to a default state, as depicted in box 200.

If photosensor detector 30 and/or processing unit 40 determine that there has been a significant or greater reduction in ambient lighting, the reduction greater than a predetermined value, or greater than a predetermined range, then device 10 enters a proximity sensing state, as depicted by box 220.

In proximity sensing state, photosensor detector 30 and/or processing unit 40 are configured to determine whether there is any light e.g., ambient light. Light source 20 may be toggled to an inactive state. In some examples, photosensor detector 30 and/or processing unit 40 are configured to determine whether the amount of light detected is below a predetermined threshold, or below a predetermined range, as depicted in diamond 230.

In proximity sensing state, light source 20 may be toggled to an active state. When light source 20 is toggled to an active state, photosensor detector 30 and/or processing unit 40 are configured to measure reflected light off of a surface, as depicted in diamond 240. Photosensor detector 30 and/or processing unit 40 may measure the proximity of device 10 to the surface from the measured reflected light, the light may be from light source 20.

If photosensor detector 30 and/or processing unit 40 determine that there is no light, e.g., no ambient light, or that the amount of ambient light is below a predetermined range, or a predetermined threshold value, the amount of light indicative that device 10 is near to a surface. And photosensor detector 30 and/or processing unit 40 determine that light reflected off of a surface is indicative of a close operating proximity, e.g., near to a surface, then device 10 may enter a proximity=OK state for a predetermined length of time, as depicted in box 250. The predetermined time may range from 0.1 to 5 seconds. In some examples, the order of operations of diamond 230 and diamond 240 may be reversed.

If photosensor detector 30 and/or processing unit 40 determine that there is light, e.g., ambient light and/or that there is ambient light above a minimal threshold of ambient light, the amount of light indicative that device 10 may be far from a surface. And/Or photosensor detector 30 and/or processing unit 40 determine that light reflected off of a surface is not indicative of a close operating proximity, e.g., device 10 is far from the surface, then device 10 may enter a the default state as depicted in box 200. In some examples, the order of operations of diamond 230 and diamond 240 may be reversed.

In some embodiments of the invention, while device 10 is in the proximity=OK state, a user may depress a trigger button within a set temporal period, the button described below, the determination of the temporal period as depicted in diamond 260.

If the trigger button is pressed in time, i.e., during a temporal period, and that temporal period falls within a predetermined amount of time, for example between 0.1 to 5 seconds, then device 10 enters a skin pigmentation state, as depicted by box 270.

If the trigger button is pressed during a temporal period, and that temporal period is outside of a predetermined amount of time, for example between 0.1 to 5 seconds, then device 10 may time out, and reverts to the default state as depicted in box 200.

In skin pigmentation detection state, as depicted by box 270, light source 20 may be toggled to an active state. Photosensor detector 30 and/or processing unit 40 may be configured to determine whether reflected light from light source 20 off of a surface indicates that the surface may be skin tissue that falls within a predefined skin tonal range, the skin tonal range may coincide with a predefined Fitzpatrick Classification range, or other classification ranges, the determination, as depicted by diamond 275.

If photosensor detector 30 and/or processing unit 40 determine that reflected light from light source 20 off of a surface indicates that the surface may be skin tissue that does not fall within a predefined skin tonal range, the skin tonal range may coincide with a predefined Fitzpatrick Classification range, or other classification ranges, then device 10 may return to default state, as depicted by box 200.

If photosensor detector 30 and/or processing unit 40 determine that reflected light from light source 20 off of a surface indicates that the surface may be skin tissue that does fall within a predefined skin tonal range, the skin tonal range may coincide with a predefined Fitzpatrick Classification range, or other classification ranges, then device 10 may emit a pulse of energy, e.g., light, as depicted in box 280.

After emitting a pulse of energy, photosensor detector 30 and/or processing unit 40 may be configured to determine if there is a change in lighting, e.g., ambient lighting, as depicted in diamond 285. If photosensor detector 30 detects an increase in ambient lighting, the increase may be above a predetermined range, and/or above a predetermined threshold value, device 10 may return to the default state, as depicted by box 200.

If photosensor detector 30 does not detect an increase in lighting, e.g., ambient lighting, and/or the increase in ambient lighting may be below a predetermined range, and/or below a predetermined threshold value, device 10 may return to proximity state 220, described above. In some examples, if photosensor detector 30 does not detect an increase in ambient lighting for a predetermined amount of time, for example 0.1 to 5 seconds, device 10 may return to proximity sensing state, as depicted by box 220.

Figure 2C:
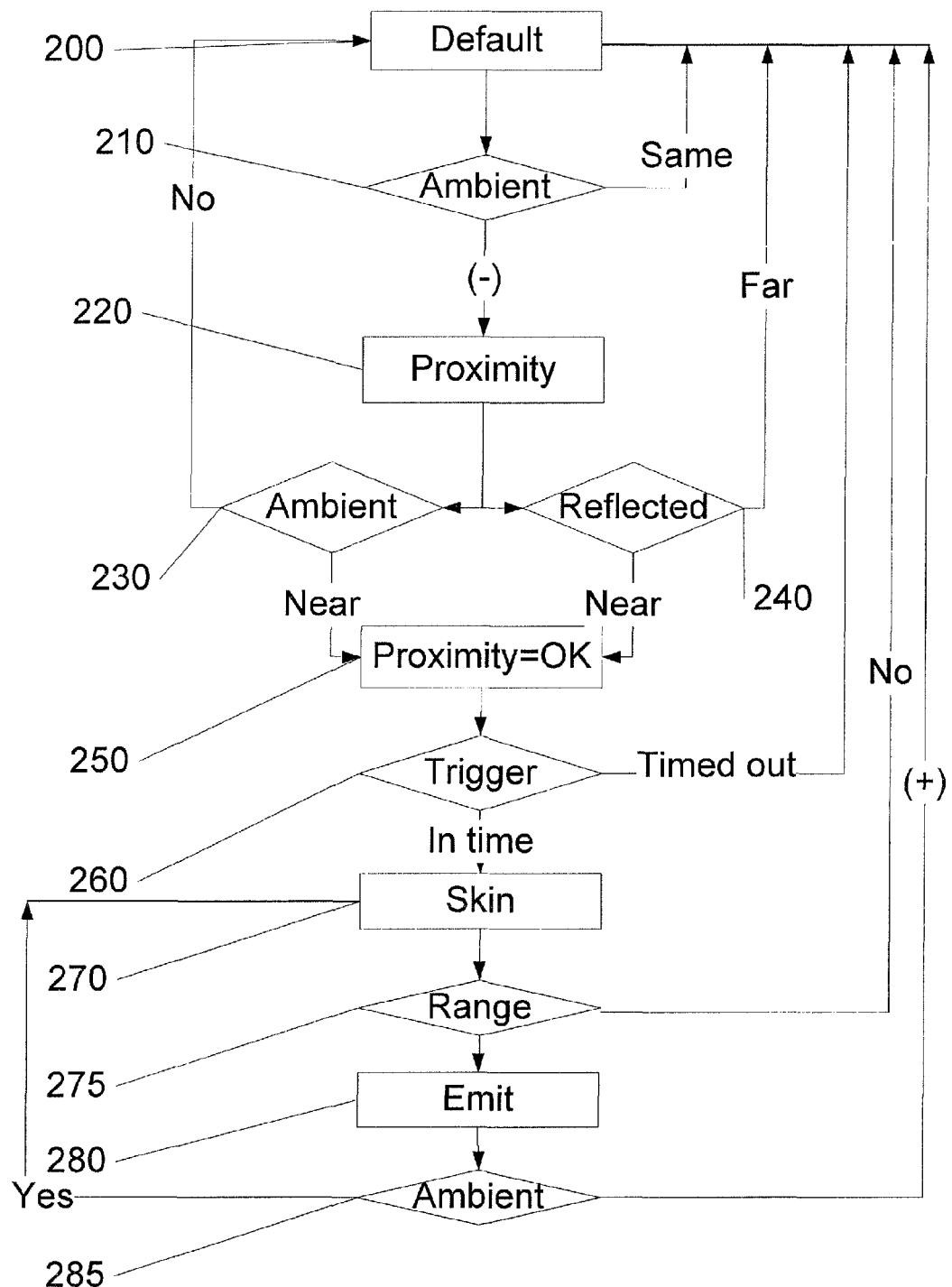
FIG. 2c is a schematic illustration of a method for using a device for dermatological use, with a failsafe control, according to an embodiment of the invention.

FIG. 2c is a schematic illustration of a method for a device for dermatological use, with a failsafe control, according to an embodiment of the invention.

Device 10 may be configured to be in a default state, as depicted by box 200. In the default state, light source 20 is toggled to the inactive state, as described above. In the default state, photosensor detector 30 is configured to monitor ambient lighting.

Photosensor detector 30 and/or processing unit 40 are configured to determine whether there has been a reduction, in some embodiments of the invention, a significant reduction, and in some embodiments of the invention, a total reduction in ambient lighting, as depicted in diamond 210.

If photosensor detector 30 and/or processing unit 40 determine that there has not been a significant reduction in ambient lighting, the reduction may be a predefined value, or may be a predefined range, device 10 remains in, and/or returns to a default state, as depicted in box 200.

If photosensor detector 30 and/or processing unit 40 determine that there has been a significant or greater reduction in ambient lighting, the reduction greater than a predetermined value, or greater than a predetermined range, then device 10 enters a proximity sensing state, as depicted by box 220.

In proximity sensing state, photosensor detector 30 and/or processing unit 40 are configured to determine whether there is any light e.g., ambient light. Light source 20 may be toggled to an inactive state. In some examples, photosensor detector 30 and/or processing unit 40 are configured to determine whether the amount of light detected is below a predetermined threshold, or below a predetermined range, as depicted in diamond 230.

In proximity sensing state, light source 20 may be toggled to an active state. When light source 20 is toggled to an active state, photosensor detector 30 and/or processing unit 40 are configured to measure reflected light off of a surface, as depicted in diamond 240. Photosensor detector 30 and/or processing unit 40 may measure the proximity of device 10 to the surface from the measured reflected light, the light may be from lights source 20.

If photosensor detector 30 and/or processing unit 40 determine that there is no light, e.g., no ambient light, or that the amount of ambient light is below a predetermined range, or a predetermined threshold value, the amount of light indicative that device 10 is near to a surface. And photosensor detector 30 and/or processing unit 40 determine that light reflected off of a surface is indicative of a close operating proximity, e.g., near to a surface, then device 10 may enter a proximity=OK state for a predetermined length of time, as depicted in box 250. The predetermined time may range from 0.1 to 5 seconds. In some examples, the order of operations of diamond 230 and diamond 240 may be reversed.

If photosensor detector 30 and/or processing unit 40 determine that there is light, e.g., ambient light and/or that there is ambient light above a minimal threshold of ambient light, the amount of light indicative that device 10 may be far from a surface. And/Or photosensor detector 30 and/or processing unit 40 determine that light reflected off of a surface is not indicative of a close operating proximity, e.g., device 10 is far from the surface, then device 10 may enter a the default state as depicted in box 200. In some examples, the order of operations of diamond 230 and diamond 240 may be reversed.

In some embodiments of the invention, while device 10 is in the proximity=OK state, a user may depress a trigger button within a set temporal period, the button described below, the determination of the temporal period as depicted in diamond 260.

If the trigger button is pressed in time, i.e., during a temporal period, and that temporal period falls within a predetermined amount of time, for example between 0.1 to 5 seconds, then device 10 enters a skin pigmentation state, as depicted by box 270.

If the trigger button is pressed during a temporal period, and that temporal period is outside of a predetermined amount of time, for example between 0.1 to 5 seconds, then device 10 may time out, and reverts to the default state as depicted in box 200.

In skin pigmentation detection state, as depicted by box 270, light source 20 may be toggled to an active state. Photosensor detector 30 and/or processing unit 40 may be configured to determine whether reflected light from light source 20 off of a surface indicates that the surface may be skin tissue that falls within a predefined skin tonal range, the skin tonal range may coincide with a predefined Fitzpatrick Classification range, or other classification ranges, the determination, as depicted by diamond 275.

If photosensor detector 30 and/or processing unit 40 determine that reflected light from light source 20 off of a surface indicates that the surface may be skin tissue that does not fall within a predefined skin tonal range, the skin tonal range may coincide with a predefined Fitzpatrick Classification range, or other classification ranges, then device 10 may return to default state, as depicted by box 200.

If photosensor detector 30 and/or processing unit 40 determine that reflected light from light source 20 off of a surface indicates that the surface may be skin tissue that does fall within a predefined skin tonal range, the skin tonal range may coincide with a predefined Fitzpatrick Classification range, or other classification ranges, then device 10 may emit a pulse of energy, e.g., light, as depicted in box 280.

After emitting a pulse of energy, photosensor detector 30 and/or processing unit 40 may be configured to determine if there is a change in ambient lighting, as depicted in diamond 285. If photosensor detector 30 detects an increase in ambient lighting, the increase may be above a predetermined range, and/or above a predetermined threshold value, device 10 may return to the default state, as depicted by box 200.

If photosensor detector 30 does not detect an increase in ambient lighting, and/or the increase in ambient lighting may be below a predetermined range, and/or below a predetermined threshold value, device 10 may return to skin pigmentation detection state, as depicted by box 270 and described above. In some examples, if photosensor detector 30 does not detect an increase in ambient lighting for a predetermined amount of time, for example 0.1 to 5 seconds, device 10 may return to skin pigmentation detection state, as depicted by box 270.

Figure 2D:
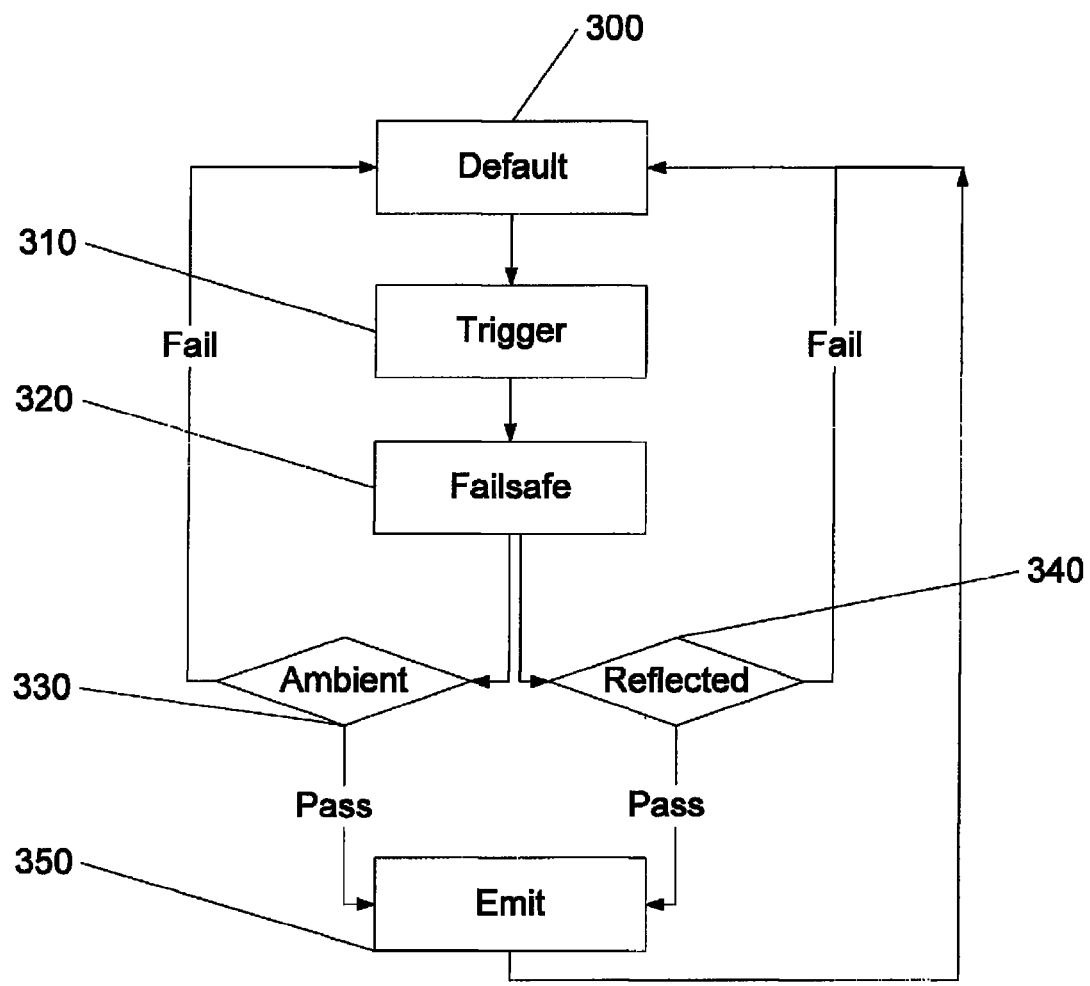
FIG. 2d is a schematic illustration of a method for using a device for dermatological use, with a failsafe control, according to an embodiment of the invention.

FIG. 2*d* is a schematic illustration of a method for a device for dermatological use, with a failsafe control, according to an embodiment of the invention.

Device 10 may be in a default state, the default state depicted by box 300.

In some embodiments of the invention, a trigger button on device 10 may be pressed as depicted in box 310. The pressing of the trigger button may start a failsafe control cascade.

In some embodiments of the invention, when trigger button is pushed device 10 the device enters a failsafe state. In the failsafe state, device 10 may be configured to determine whether the device is operating under safe conditions, e.g., within a safe operating distance to the skin of a user and in some examples on a threshold range of skin pigmentation of the user, as described above. This failsafe state as depicted by box 320. While in a failsafe state, device 10 or a component thereof may toggle light source 20 to an inactive state. When light source 20 is in an inactive state, photosensor detector 30 and/or processing unit 40 may be configured to measure light, as depicted in diamond 330. The light may be ambient lighting in the environment of device 10.

If photosensor detector 30 and/or processing unit 40 determine that light is below a predetermined threshold, or below a predetermined range of values, device 10 may not be deactivated.

If photosensor detector 30 and/or processing unit 40 determine that light is above a predetermined threshold or a range of values, device 10 may exit the failsafe state and reenter the default state, as depicted as box 300.

In failsafe state, depicted as box 320 and described above, light source 20 may be toggled to an active state, While light source 20 is in an active state, photosensor detector 30 and/or processing unit 40 may be configured to measure reflected light, as depicted in diamond 340, the measuring of reflected light may be employed to determine proximity of device 10 to a surface, e.g., a user's skin tissue, and/or to determine if the user's skin tissue falls within an actionable skin tonal range as described above.

If photosensor detector 30 and/or processing unit 40 determines that device 10 is not within a safe proximity to a surface and/or that a user's skin tissue falls outside an actionable skin tonal range, and/or the level of light detected is above a predetermined threshold or a range of values, device 10 may exit the failsafe state and reenter the default state, as depicted as box 300.

In some embodiments of the invention, device 10 may first measure ambient light, as depicted by diamond 330 and then measure reflected light, as depicted by box 340. In some embodiments of the inventions, device 10 may first measure reflected light, as depicted by box 340, and then measure ambient light, as depicted in diamond 330.

If photosensor detector 30 and/or processing unit 40 determines that device 10 is within proximity to a surface and that a user's skin tissue falls within an actionable skin tonal range, and that ambient light is below a threshold value, or a threshold range of values, then the device 10, or a component thereof configured to determine if device 10 has passed the failsafe controls, will cause an active component to emit a pulse or a plurality of pulses of energy, e.g. light, as depicted in box 350.

Once a pulse or a plurality of pulses of energy have been emitted, device 10 will revert back to default state, as depicted by box 300.

Figure 2E:
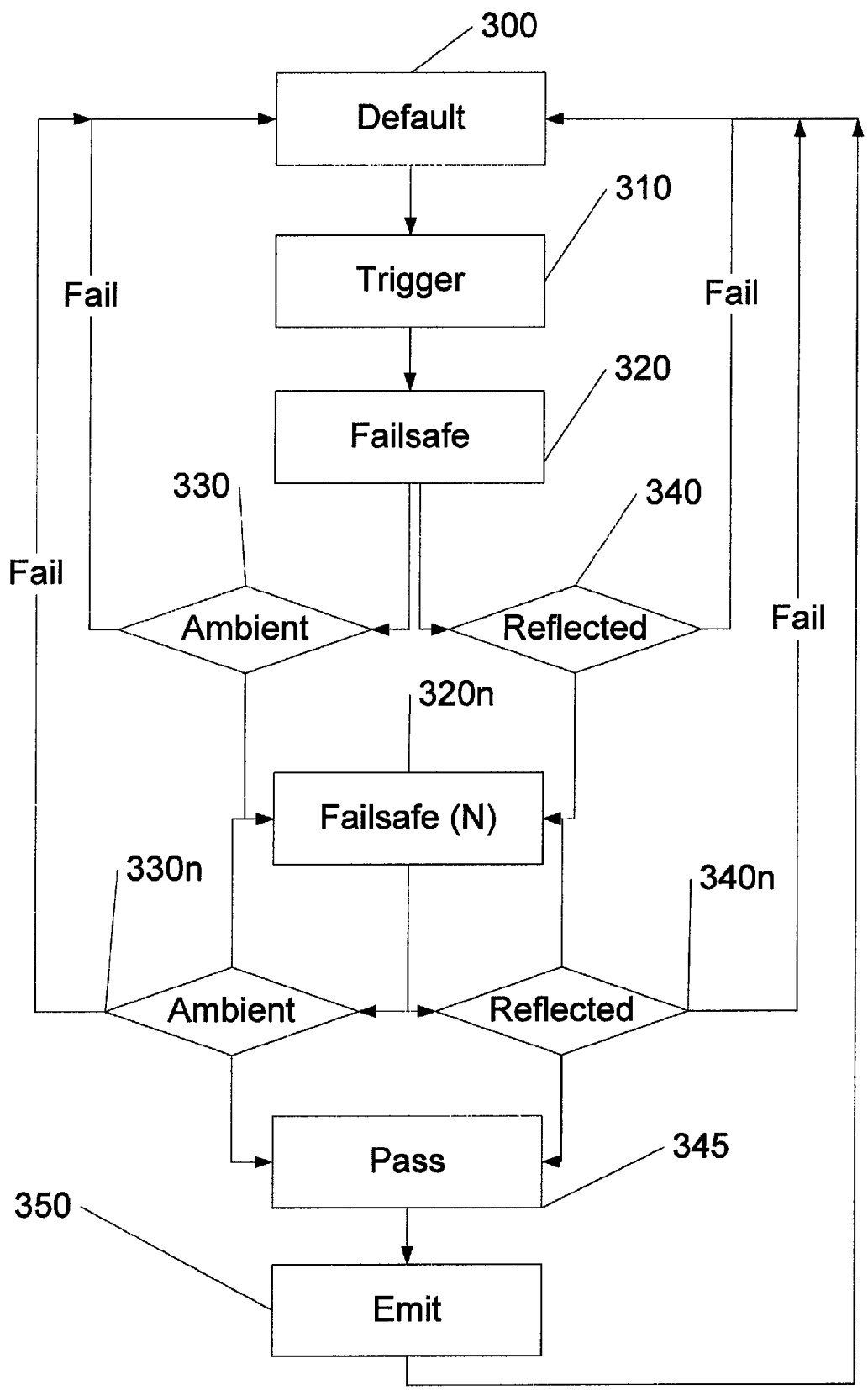
FIG. 2e is a schematic illustration of a method for using a device for dermatological use, with a failsafe control, according to an embodiment of the invention.

FIG. 2e is a schematic illustration of a method for a device for dermatological use, with a failsafe control, according to an embodiment of the invention.

Device 10 may be in a default state, the default state depicted by box 300.

In some embodiments of the invention, a trigger button on device 10 may be pressed as depicted in box 310.

When trigger button is pushed, device 10 the device may enter a failsafe state. In the failsafe state, device 10 may be configured to determine whether the device is operating under safe condition, e.g., within a safe operating distance to the skin of a user and in some examples on a threshold range of skin pigment, as described above. This failsafe step as depicted by box 320. While in a failsafe state, device 10 or a component thereof may toggle light source 20 to an inactive state. When light source 20 is in an inactive state, photosensor detector 30 and/or processing unit 40 may be configured to measure light, as depicted in diamond 330.

If photosensor detector 30 and/or processing unit 40 determine that light is below a predetermined threshold, or below a predetermined range of values, device 10 may not be deactivated.

If photosensor detector 30 and/or processing unit 40 determine that light is above a predetermined threshold or a range of values, device 10 may exit the failsafe state and reenter the default state, as depicted as box 300.

In failsafe state, depicted as box 320 and described above, light source 20 may be toggled to an active state, While light source 20 is in an active state, photosensor detector 30 and/or processing unit 40 may be configured to measure reflected light, as depicted in diamond 340, the measuring of reflected light may be employed to determine proximity of device 10 to a surface, e.g., a user's skin tissue, and to determine if the user's skin tissue falls within an actionable skin tonal range as described above.

If photosensor detector 30 and/or processing unit 40 determines that device 10 is not within a safe proximity to a surface and/or that a user's skin tissue falls outside an actionable skin tonal range, and/or the level of light detected is above a predetermined threshold or a range of values, device 10 may exit the failsafe state and reenter the default state, as depicted as box 300.

In some embodiments of the invention, device 10 may first measure ambient light, as depicted by diamond 330 and then measure reflected light, as depicted by box 340. In some embodiments of the inventions, device 10 may first measure reflected light, as depicted by box 340, and then measure ambient light, as depicted in diamond 330.

If photosensor detector 30 and/or processing unit 40 determines that device 10 is within proximity to a surface and that a user's skin tissue falls within an actionable skin tonal range, and that ambient light is below a threshold value, or a threshold range of values, then the device 10 will move to do additional failsafe controls, as depicted by box 320*n*.

Device 10 may be configured to cycle through a predetermined number of failsafe controls including a predetermined number of measurements of ambient lighting as depicted by diamond 330*n* and a predetermined measurement of reflections, as depicted by diamond 340*n*.

Once device 10 has cycled successfully through a plurality of failsafe controls, the number of cycles may be predetermined, and may range from 1 to 10 cycles, in some examples, there may be more cycles, device 10 may enter into a passed state, as depicted by box 345. Once in the passed state, device 10 may be configured to emit one or a plurality of pulses of energy, e.g., light. Once a pulse or a plurality of pulses of energy has been emitted, device 10 will revert back to default state, as depicted by box 300.

Figure 3:
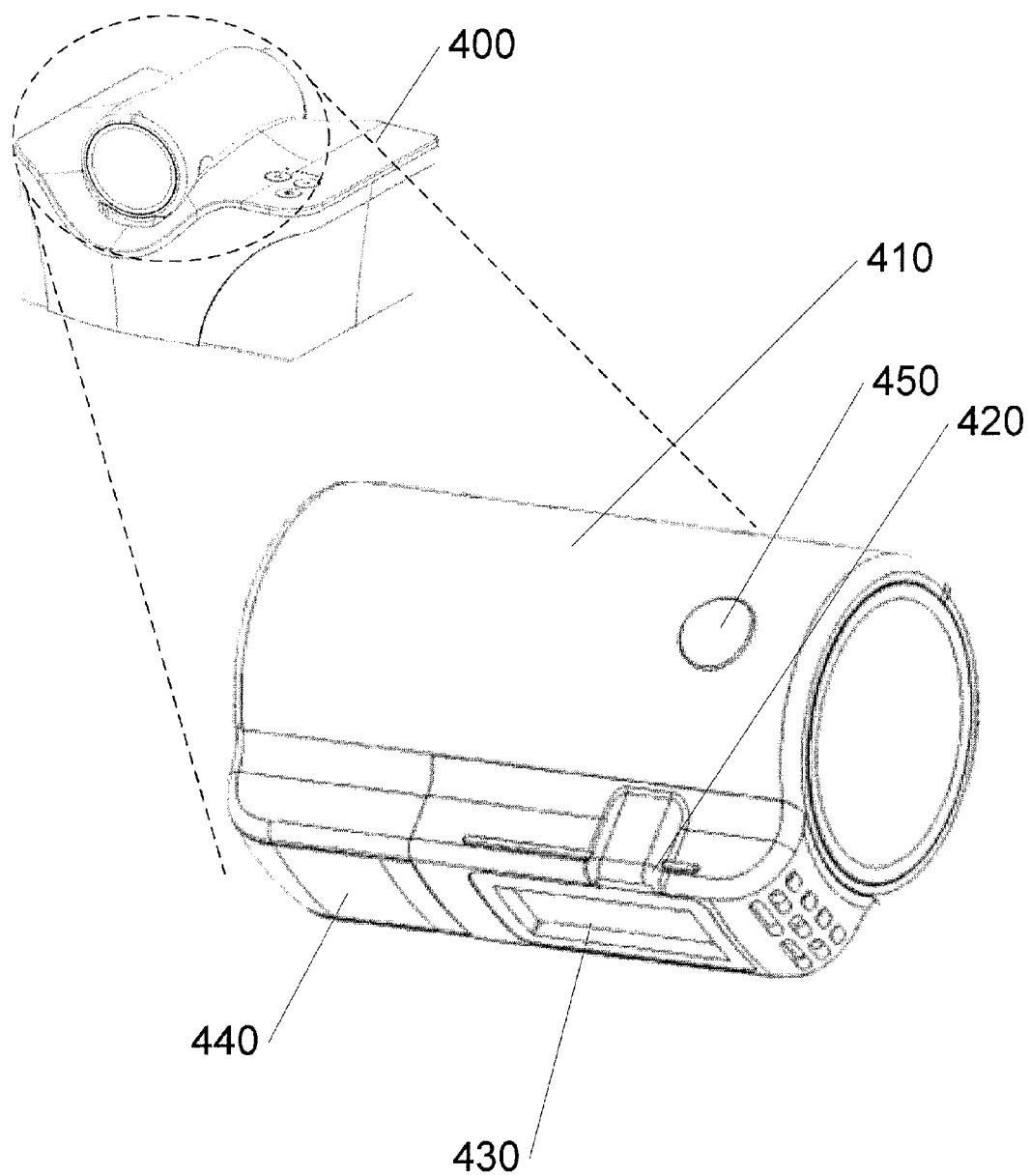
FIG. 3 is a schematic illustration of a device for dermatological use, with a failsafe control, according to an embodiment of the invention; and, FIG. 4 is a schematic illustration of a method for a device for dermatological use, with a failsafe control, according to an embodiment of the invention.

FIG. 3 is a schematic illustration of a device for dermatological use, with a failsafe control, according to an embodiment of the invention.

In some embodiments of the invention, device 410 may be a dermatological device. Device 410 may be a dermatological device for use in medical and/or cosmetic treatments. Device 410 may be a dermatological device for use at home by a lay person and/or for use in a clinic, spa, salon, medical, and/or other setting for use by a person with some training in the use of the device.

Device 410 may have an active component 430. The active component may be a light source for use in IPL treatment. Active component 430 may be a laser, or a transmitter, and/or emitter of a form of energy and/or radiation.

Device 310 may have a base 400. Base 400 may charge device 410, may provide a cradle for storing device 410, and may provide a storage unit for storing components of device 410, for example, for storing power cords, filters, batteries, extra active components 430, and or other components associated with device 310.

Device 410 may have a light source 420, the light source may be configured to be toggled between an activated state and an inactivated state. Light source 420 may be used, as described above with reference to light source 20, to determine proximity of device 410 to a user and/or to determine the nature of the skin tissue in proximity to device 410, e.g., a skin tonal range. Skin tonal range may reflect values and measurements related to the Fitzpatrick Classification, the Von Luschan's chromatic scale or other pigmentations ranges, as described above.

In some embodiments of the invention, a safe operating skin tonal range may be a subset of the tonal ranges described and/or delimited in the Fitzpatrick Classification Scale, the Von Luschan's chromatic scale or other scales and ranges of skin pigmentation.

Device 410 may have a photosensitive detector 440, the photosensitive detector configured to detect ambient light, light emitted from light source 420 and/o reflections of light off of a surface, the surface may be in close proximity to photosensor 440, as described above.

Device 410 may have a trigger 450, the trigger configured to allow a user to enable the active component 430 to deliver one or a plurality of pulses of energy.

Figure 4:
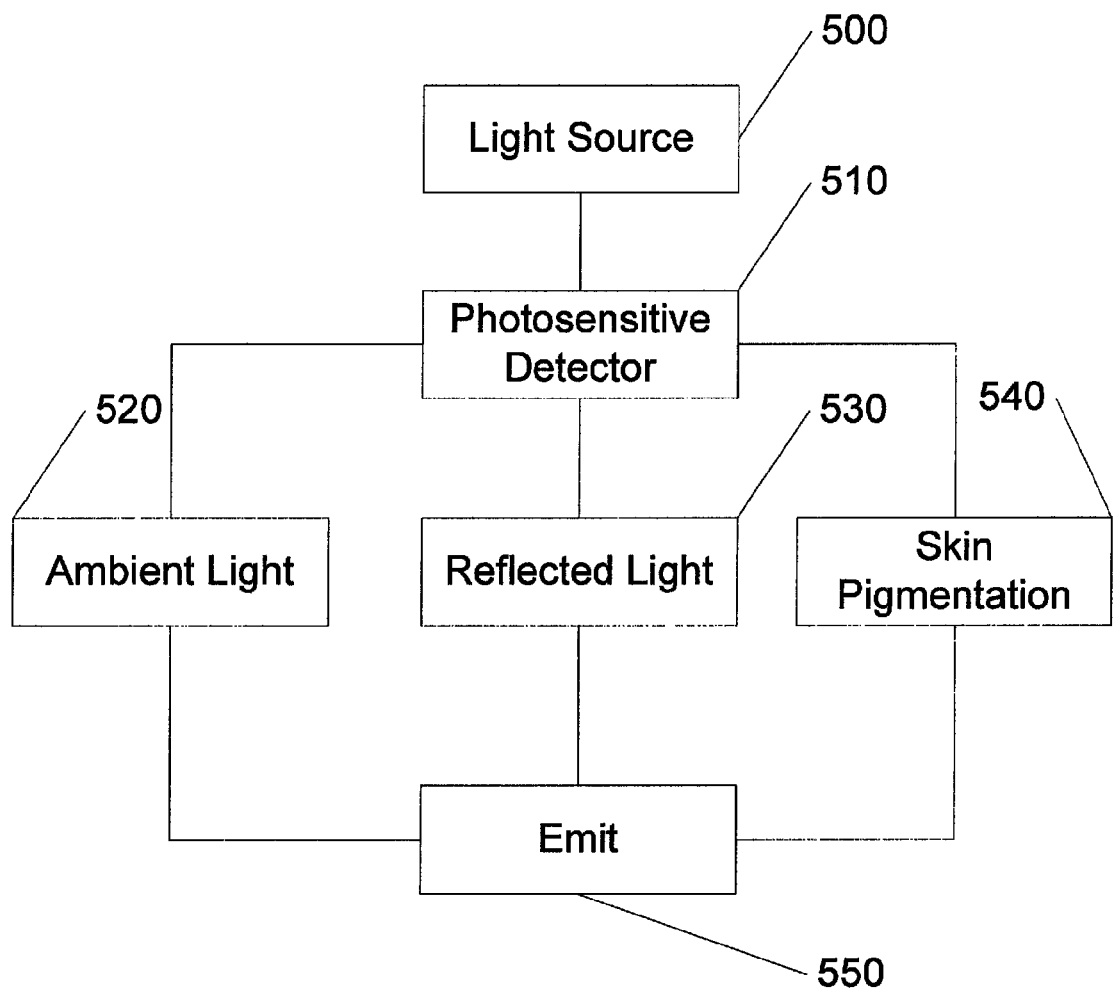

FIG. 4 is a schematic illustration of a method for a device for dermatological use, with a failsafe control, according to an embodiment of the invention.

The method may include the use of a device for dermatological use with one or a plurality of active components and a failsafe control, the method may include the following steps.

Device 10 may have a light source, the light source may be configured to be toggled between an activated state and an inactivated state, as depicted in box 500.

Device 10 may have a photosensitive detector, the photosensitive detector may be configured to detect incoming light as depicted in box 510.

Device 10 may have a processing unit, the method may include configuring a processing unit to concurrently determine whether ambient light detected by the photosensitive detector is indicative of a safe operating proximity of the device to a surface, as depicted in box 520. And determine whether light reflected from the surface and received by the photosensitive detector is indicative of a safe operating distance from the surface, as depicted in box 530. And determine whether light reflected from the surface and received by the photosensitive detector is indicative of a safe operating skin tonal range as depicted in box 540.

Device 10 may have an active component, the active component may be configured, in the method, to be activated and emit light only when the processing unit determines that the device is within the safe operating proximity, and that the light reflected from the surface is indicative of the safe operating skin tonal range, as depicted by box 550.

Examples of the present invention may include apparatuses for performing the operations described herein. Such apparatuses may be specially constructed for the desired purposes, or may comprise computers or processors selectively activated or reconfigured by a computer program stored in the computers. Such computer programs may be stored in a computer-readable or processor-readable non-transitory storage medium, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions. It will be appreciated that a variety of programming languages may be used to implement the teachings of the invention as described herein. Examples of the invention may include an article such as a non-transitory computer or processor readable non-transitory storage medium, such as for example, a memory, a disk drive, or a USB flash memory encoding, including or storing instructions, e.g., computer-executable instructions, which when executed by a processor or controller, cause the processor or controller to carry out methods disclosed herein. The instructions may cause the processor or controller to execute processes that carry out methods disclosed herein.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A device for dermatological use with one or a plurality of active components and a failsafe control, the failsafe control comprising:
    a light source configured to be toggled between an activated state and an inactivated state;
    a photosensitive detector configured to detect incoming light; and
    a processing unit configured to concurrently:
        monitor ambient lighting detected by the photosensitive detector when the light source is in the inactivated state, to determine whether the device is in close contact with a surface, which is indicative of a safe operating proximity of the device to the surface;
        determine whether light from the light source in the activated state, which was reflected from the surface is detected by the photosensitive detector is indicative of a safe operating proximity of the device to the surface;
        determine whether light from the light source in the activated state, which was reflected from the surface and received detected by the photosensitive detector falls within a predefined skin tonal range; and
        activate said one or a plurality of active components only upon the processing unit determining that the device is within the safe operating proximity, and that the light from the light source in the activated state, reflected from the surface is detected and indicative of the safe operating skin tonal range.

2. The device of claim 1, wherein a single light source provides both the light reflected from the surface and detected by the photosensitive detector for determining a safe operating proximity of the device to the surface, and the light reflected from the surface and detected by the photosensitive detector for determining a safe operating skin tonal range.

3. The device of claim 1, wherein the processing unit is configured to accept a signal from a trigger configured to be depressed within a set temporal period before the processing unit determines whether light reflected from the surface is detected by the photosensitive detector, and whether the light reflected from the surface and detected by the photosensitive detector is indicative of a safe operating skin tonal range.

4. The device of claim 1, wherein activating said one or a plurality of active components results in the device delivering a set of pulses of energy to the surface.

5. The device of claim 1, wherein the processing unit of the failsafe control is further configured, after activating said one or a plurality of active components, to
    further monitor ambient lighting detected by the photosensitive detector when the light source is in the inactivated state, to determine whether the device is in close contact with a surface, that is indicative of a safe operating proximity of the device to a surface;
    whether light, when the light source in the activated state, reflected from the surface is detected by the photosensitive detector; and,
    whether light, when the light source in the activated state, reflected from the surface and detected by the photosensitive detector falls within a predetermined a safe operating skin tonal range before activating said one or a plurality of active components again.

6. The device of claim 1, wherein the processing unit for the failsafe control is further configured, after activating said one or a plurality of active components, to:
    determine whether light detected by the photosensitive detector is indicative of a safe operating proximity of the device to a surface, and
configured to determine whether light reflected from the surface and received detected by the photosensitive detector falls within a predetermined a safe operating skin tonal range before activating said one or a plurality of active components again.

7. The device of claim 1, wherein the processing unit for the failsafe control is configured to:
    determine whether, when the light source is in the inactivated state, light reflected from the surface and detected by the photosensitive detector is indicative of a safe operating skin tonal range; and
    determine whether light, when the light source is in the activated state, detected by the photosensitive detector is indicative of a safe operating proximity of the device to a surface and determine whether light reflected from the surface and detected by the photosensitive detector is indicative of a safe operating proximity of the device to the surface.

8. The device of claim 1, wherein the processing unit for the failsafe control is configured to iteratively
　determine whether light, when the light source is in the inactivated state, reflected from the surface and detected by the photosensitive detector falls within a predetermined a safe operating skin tonal range; and
　concurrently determine whether light, when the light source is in the activated state, detected by the photosensitive detector is indicative of a safe operating proximity of the device to a surface and determine whether light reflected from the surface and detected by the photosensitive detector is indicative of a safe operating proximity of the device to the surface.

9. The device of claim 1, wherein the device is configured for home use.

10. The device of claim 1, wherein the device is configured for cosmetic use.

11. The device of claim 1, wherein the active component is configured to provide intense pulsed light therapy.

12. The device of claim 1, wherein the active component is configured to provide laser therapy.

13. The device of claim 1, further configured to block activation of the device until light detected while the light source is in the inactivated state indicates changes in proximity to the skin.

14. The device of claim 1 further comprising a trigger for activating the failsafe control.

15. A method for use of a device for dermatological use with one or a plurality of active components and a failsafe control, the method comprising:
　configuring a failsafe device comprising
　configuring a light source to be toggled between an activated state and an inactivated state;
　configuring a photosensitive detector to detect incoming light; and
　configuring a processing unit to concurrently:
　　determine whether ambient light detected by the photosensitive detector, when the light source is in the inactivated state, is indicative of the device being in close contact with a surface, and indicative of a safe operating proximity of the device to a that surface;
　　determine whether light, when the light source is in the activated state, reflected from the surface is detected by the photosensitive;
　　determine whether light from the light source in the activated state reflected from the surface and detected by the photosensitive detector falls within a predefined skin tonal range; and
　　activate said one or a plurality of active components only upon the processing unit determining that the device is within the safe operating proximity, and that the light from the light source in the activated state, reflected from the surface is detected and indicative of the safe operating skin tonal range.

16. The method of claim 15, wherein the device is configured for home use.

17. The method of claim 15, wherein the device is configured for cosmetic use.

18. The method of claim 15, wherein said one or a plurality of active components is configured to provide intense pulsed light therapy.

19. The method of claim 15, wherein said one or a plurality of active components is configured to provide laser therapy.

20. A failsafe control for a device, the failsafe control comprising:
　a light source, the light source configured to be togglable to an activated and inactivated state;
　a photosensitive detector configured to measure ambient lighting and reflections;
　a processing unit configured to activate the device when detected ambient lighting and reflections indicate a safe operation of the device; and,
　the processing unit further configured to deactivate the device when ambient lighting or reflections indicate an unsafe operation of the device.

* * * * *